(12) United States Patent
Salman et al.

(10) Patent No.: US 10,205,925 B2
(45) Date of Patent: Feb. 12, 2019

(54) WHITE BALANCE ENCLOSURE FOR USE WITH A MULTI-VIEWING ELEMENTS ENDOSCOPE

(71) Applicant: EndoChoice, Inc., Alpharetta, GA (US)

(72) Inventors: Golan Salman, Atlit (IL); Victor Levin, Haifa (IL); Yaniv Kirma, Karcur (IL); Yuri Gershov, Haifa (IL)

(73) Assignee: EndoChoice, Inc., Alpharetta, GA (US)

(*) Notice: Subject to any disclaimer, the term of this patent is extended or adjusted under 35 U.S.C. 154(b) by 0 days.

(21) Appl. No.: 15/493,007

(22) Filed: Apr. 20, 2017

(65) Prior Publication Data

US 2017/0280979 A1 Oct. 5, 2017

Related U.S. Application Data

(63) Continuation of application No. 14/271,234, filed on May 6, 2014, now Pat. No. 9,667,935.

(60) Provisional application No. 61/820,650, filed on May 7, 2013.

(51) Int. Cl.
*H04N 9/73* (2006.01)
*A61B 1/00* (2006.01)
*A61B 1/045* (2006.01)

(52) U.S. Cl.
CPC ......... *H04N 9/735* (2013.01); *A61B 1/00057* (2013.01); *A61B 1/00177* (2013.01); *A61B 1/00181* (2013.01); *A61B 1/045* (2013.01)

(58) Field of Classification Search
None
See application file for complete search history.

(56) References Cited

U.S. PATENT DOCUMENTS

| | | | |
|---|---|---|---|
| 3,639,714 | A | 2/1972 | Fujimoto |
| 3,955,064 | A | 5/1976 | Demetrio |
| 4,027,697 | A | 6/1977 | Bonney |
| 4,037,588 | A | 7/1977 | Heckele |
| 4,084,401 | A | 4/1978 | Belardi |
| 4,402,313 | A | 9/1983 | Yabe |
| 4,461,282 | A | 7/1984 | Ouchi |
| 4,494,549 | A | 1/1985 | Namba |

(Continued)

FOREIGN PATENT DOCUMENTS

| | | |
|---|---|---|
| CA | 2297986 | 3/1999 |
| CA | 2765559 | 12/2010 |

(Continued)

OTHER PUBLICATIONS

International Search Report for PCT/US14/37004, dated Sep. 25, 2014.

(Continued)

*Primary Examiner* — Hung Q Dang
(74) *Attorney, Agent, or Firm* — Bookoff McAndrews, PLLC

(57) ABSTRACT

The specification describes a white balance enclosure for use with a tip of a multi-viewing elements endoscope. The white balance enclosure is used to provide a reference white background to the plurality of viewing elements when the tip is positioned within the white balance enclosure and a white balance circuit is used to calculate and store reference white balance values based on white field/test feed signals generated by the plurality of viewing elements exposed to the reference white background.

18 Claims, 10 Drawing Sheets

(56) References Cited

U.S. PATENT DOCUMENTS

| | | |
|---|---|---|
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,111,804 A | 5/1992 | Funakoshi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | EbbesmeierneeSchitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 * | 8/2001 | Yoon ................ A61B 1/00177 600/104 |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Stelzer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 * | 3/2004 | Ueno ................ A61B 1/00009 348/70 |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |

(56) References Cited

U.S. PATENT DOCUMENTS

| | | |
|---|---|---|
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | Mccutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takata |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1* | 3/2012 | Levy ................. A61B 1/00177 600/109 |
| 2012/0057251 A1 | 3/2012 | Takata |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |

(56) References Cited

U.S. PATENT DOCUMENTS

| | | |
|---|---|---|
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1* | 7/2013 | Ono ............ A61B 1/045 348/234 |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184765 A1* | 7/2014 | King ............ H04N 7/18 348/65 |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | 61-126221 | 8/1986 |
| JP | 2000-342530 | 3/1991 |
| JP | H1043129 | 2/1998 |
| JP | H10239740 | 9/1998 |
| JP | 11137512 | 5/1999 |
| JP | 2003140056 | 5/2003 |
| JP | 2005253543 | 9/2005 |
| JP | 2006025888 | 2/2006 |
| JP | 2006068109 | 3/2006 |
| JP | 2006325690 | 12/2006 |
| JP | 2006334112 | 12/2006 |

(56) References Cited

FOREIGN PATENT DOCUMENTS

| | | | | |
|---|---|---|---|---|
| JP | 2007215764 | | 8/2007 | |
| JP | 2010178766 | A | 8/2010 | |
| JP | 2012135432 | | 7/2012 | |
| JP | 2013116277 | A2 | 6/2013 | |
| JP | 2013123647 | | 6/2013 | |
| JP | 2013123648 | | 6/2013 | |
| JP | 2013208459 | | 10/2013 | |
| JP | 2013215582 | | 10/2013 | |
| JP | 2013230383 | | 11/2013 | |
| JP | 2013542467 | | 11/2013 | |
| JP | 2013544617 | | 12/2013 | |
| JP | 2014524303 | | 9/2014 | |
| JP | 2014524819 | | 9/2014 | |
| JP | 2015533300 | | 11/2015 | |
| TM | 2014182723 | | 11/2014 | |
| WO | 2006073676 | | 7/2006 | |
| WO | 2006073725 | | 7/2006 | |
| WO | 2007070644 | | 6/2007 | |
| WO | 2007092533 | | 8/2007 | |
| WO | 2007092636 | | 8/2007 | |
| WO | 2007087421 | | 11/2007 | |
| WO | 2007136859 | | 11/2007 | |
| WO | 2007136879 | | 11/2007 | |
| WO | 2008015164 | | 2/2008 | |
| WO | 2009014895 | | 1/2009 | |
| WO | 2009015396 | | 1/2009 | |
| WO | 2009049322 | | 4/2009 | |
| WO | 2009049324 | | 4/2009 | |
| WO | 2009062179 | | 5/2009 | |
| WO | 2010146587 | A1 | 12/2010 | |
| WO | 2012038958 | | 3/2012 | |
| WO | WO 2012/038958 | A2 * | 3/2012 | ......... A61B 1/00091 |
| WO | 2012056453 | A2 | 5/2012 | |
| WO | 2012075153 | A2 | 6/2012 | |
| WO | 2012077116 | | 6/2012 | |
| WO | 2012077117 | A1 | 6/2012 | |
| WO | WO 2012/077117 | A1 * | 6/2012 | ......... A61B 1/00091 |
| WO | 2012096102 | | 7/2012 | |
| WO | 2012120507 | A1 | 9/2012 | |
| WO | 2013014673 | | 1/2013 | |
| WO | 2013024476 | | 2/2013 | |
| WO | 2014061023 | | 4/2014 | |
| WO | 2014160983 | | 10/2014 | |
| WO | 2014179236 | | 11/2014 | |
| WO | 2014182728 | | 11/2014 | |
| WO | 2014183012 | | 11/2014 | |
| WO | 2014186230 | | 11/2014 | |
| WO | 2014186519 | | 11/2014 | |
| WO | 2014186521 | | 11/2014 | |
| WO | 2014186525 | | 11/2014 | |
| WO | 2014186775 | | 11/2014 | |
| WO | 2014210516 | | 12/2014 | |
| WO | 2015002847 | | 1/2015 | |
| WO | 2015047631 | | 4/2015 | |
| WO | 2015050829 | | 4/2015 | |
| WO | 2015084442 | | 6/2015 | |
| WO | 2015095481 | | 6/2015 | |
| WO | 2015112747 | | 7/2015 | |
| WO | 2015112899 | | 7/2015 | |
| WO | 2015134060 | | 9/2015 | |
| WO | 2015168066 | | 11/2015 | |
| WO | 2015168664 | | 11/2015 | |
| WO | 2015171732 | | 11/2015 | |
| WO | 2015175246 | | 11/2015 | |
| WO | 2016014581 | | 1/2016 | |
| WO | 2016033403 | | 3/2016 | |

OTHER PUBLICATIONS

International Search Report for PCT/US14/38094, dated Nov. 6, 2014.
International Search Report for PCT/US2014/037526, dated Oct. 16, 2014.
International Search Report for PCT/US2014/071085, dated Mar. 27, 2015.
International Search Report for PCT/US2014/58143, dated Jan. 21, 2015.
International Search Report for PCT/US2015/012506, dated Dec. 11, 2015.
International Search Report for PCT/US2015/012751, dated Jun. 26, 2015.
International Search Report for PCT/US2015/027902, dated Jul. 23, 2015.
International Search Report for PCT/US2015/28962, dated Jul. 28, 2015.
International Search Report for PCT/US2015/29421, dated Aug. 7, 2015.
International Search Report for PCT/US2015/41396, dated Sep. 29, 2015.
International Search Report for PCT/US2015/47334, dated Dec. 28, 2015.
International Search Report for PCT/US2015/6548, dated Feb. 26, 2016.
International Search Report for PCT/US2015/66486, dated Dec. 17, 2015.
Office Action date Feb. 26, 2016 for U.S. Appl. No. 14/274,323.
Office Action dated Feb. 4, 2016 for U.S. Appl. No. 14/271,234.
Office Action dated May 25, 2016 for U.S. Appl. No. 14/271,234.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 5, 2016 for U.S. Appl. No. 14/278,338.
Office Action dated May 6, 2016 for U.S. Appl. No. 14/263,896.
Office Action dated Jun. 28, 2016 for U.S. Appl. No. 14/278,293.
Office Action dated Jun. 30, 2016 for U.S. Appl. No. 13/655,120.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Office Action dated Aug. 11, 2016 for U.S. Appl. No. 14/318,249.
Sherman L.M., Plastics That Conduct Hear, Plastics Technology, Jun. 2001—article obtained online from http://www.ptonline.com/articles/plastics-that-conduct-heat.
Notice of Allowance dated Jan. 31, 2017 for U.S. Appl. No. 14/271,234.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Extended European Search Report for EP14794424.3, dated Nov. 22, 2016.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.

(56) References Cited

OTHER PUBLICATIONS

Office Action dated Dec. 30, 2016 for U.S. Appl. No. 14/457,268.
First Office Action for Chinese Patent Application No. 201480038565.7, dated Dec. 8, 2016.
Office Action dated Jan. 17, 2017 for U.S. Appl. No. 14/318,189.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.

\* cited by examiner

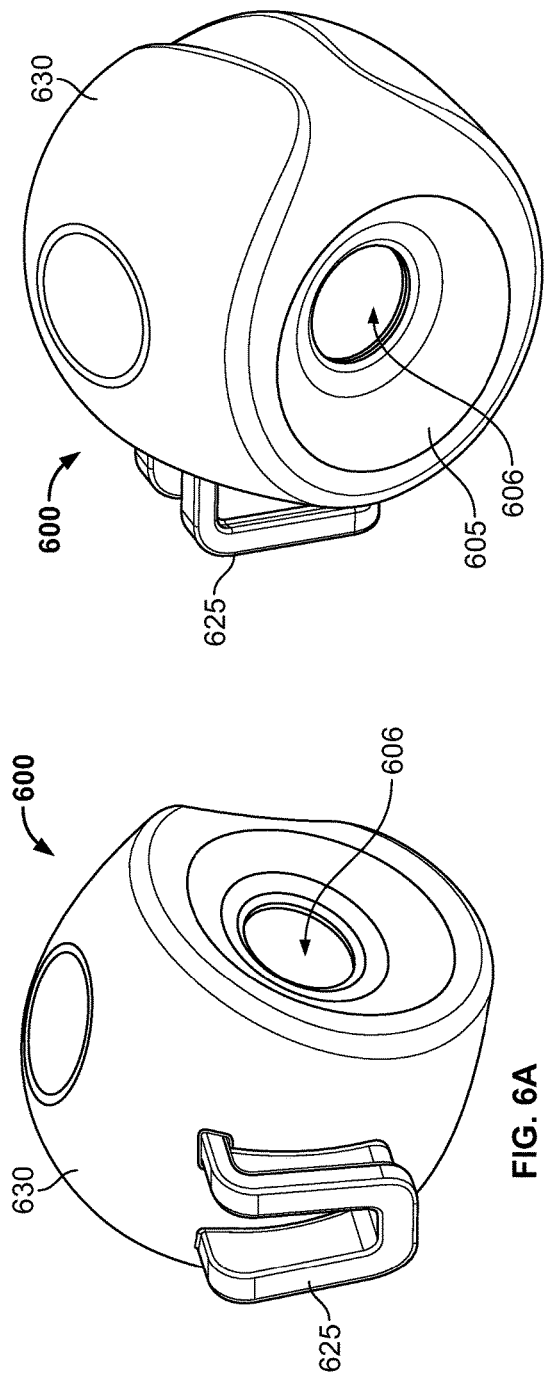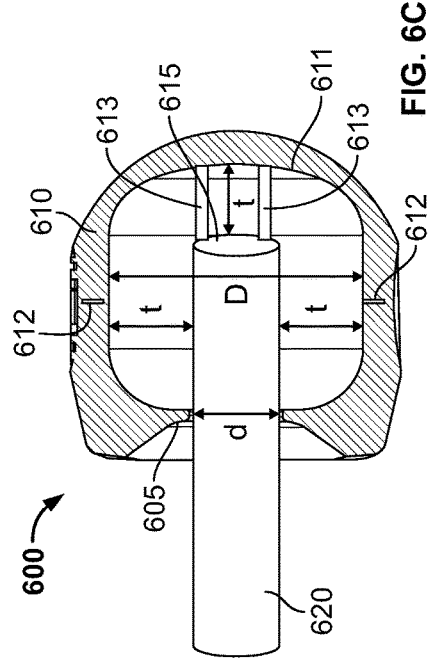

WHITE BALANCE ENCLOSURE FOR USE WITH A MULTI-VIEWING ELEMENTS ENDOSCOPE

CROSS REFERENCE

The present application is a continuation application of U.S. patent application Ser. No. 14/271,234, entitled "White Balance Enclosure for Use with a Multi-Viewing Elements Endoscope" and filed on May 6, 2014, which relies on U.S. Provisional Patent Application No. 61/820,650, of the same title and filed on May 7, 2013, for priority.

The present application is also related to U.S. patent application Ser. No. 14/263,896, entitled "Video Processing In A Compact Multi-Viewing Element Endoscope System" and filed on Apr. 28, 2014 and to U.S. Provisional Patent Application No. 61/936,562, entitled "Method and System for Video Processing In A Multi-Viewing Element Endoscope" and filed on Feb. 6, 2014.

All of the above mentioned applications are herein incorporated by reference in their entirety.

FIELD

The present specification generally relates to a multi-viewing elements endoscope, and more particularly to a white balancing enclosure, designed as a cap in one embodiment, for consistently and uniformly applying a white balance adjustment to a picture image or video generated by multiple viewing elements.

BACKGROUND

An endoscope conventionally comprises an elongated tubular shaft, rigid or flexible, having a video camera and/or fiber optic lens assembly at its distal end. The shaft is connected to a handle and viewing is made possible via an external screen. Various surgical tools may be inserted through a working channel in the endoscope for performing different surgical procedures.

Endoscopes, such as colonoscopes, that are currently being used typically have a front camera for viewing the internal organ, such as the colon, an illuminator, a fluid injector for cleaning the camera lens, and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics, which transmit light generated remotely, to the endoscope tip section.

The inside of internal organs such as the stomach, colon or cecum is generally reddish. As a result, when internal organs are observed using an endoscope without having appropriate color adjustment of picture image or video signals, the captured color images and videos carry a substantially reddish hue. In a conventional endoscope, in order to prevent this problem, a white balance adjustment is carried out; that is, values, factors or coefficients for making the intensity of the picture image or video signals for three primary colors such as red (R), green (G) and blue (B) equal, are applied to the video signal generated from a camera. In addition, white balance adjustment is also performed to make the intensity of the picture image or video signals for four additional colors, such as yellow (Ye), cyan (Cy), magenta (Mg), and green (G), equal for charge coupled device (CCD) sensor based processes. Such values, factors, or coefficients are generated by imaging a reference white color object.

However, for a multi-viewing elements endoscope, all cameras need to be calibrated for white balance consistently and uniformly. There is thus a need in the art for enabling consistent and uniform white balance calibration of all viewing elements of a multi-viewing elements endoscope. There is also a need in the art for a novel and easy to use reference white object that exposes all viewing elements of a multi-viewing elements endoscope to the same reference white level for purposes of white balance calibration.

SUMMARY

The following embodiments and aspects thereof are described and illustrated in conjunction with systems, tools and methods, which are meant to be exemplary and illustrative, not limiting in scope.

In accordance with an embodiment of the present specification, a tip section of a multi-viewing element endoscope comprises at least one front-pointing viewing element and at least one front illuminator associated therewith; at least one side-pointing viewing element and at least one side illuminator associated therewith; a front working channel configured for insertion of a medical tool; and at least one side service channel configured for insertion of medical tools. The multi-viewing element endoscope is connected to a main control unit that governs a plurality of operational functionalities of the endoscope. At least one display may be connected to the main control unit and configured to display images and/or video streams received from the viewing elements of the multi-viewing element endoscope.

In some embodiments, each of the front-pointing viewing element and the at least one side-pointing viewing element comprises an image sensor such as, but not limited to, a charge coupled device (CCD) or a complementary metal oxide semiconductor (CMOS).

In one embodiment, the camera board of the main control unit circuit board outputs video feeds, received from the multiple viewing elements of the endoscope, to a white balancing circuit. In one embodiment, the endoscope tip comprises three viewing elements (one front-looking and two side-looking viewing elements). Therefore, in one embodiment, the output video feeds comprise three video feeds corresponding to the three viewing elements of the endoscope.

In one embodiment, a white balance circuit is implemented as part of the field-programmable gate array (FPGA) on the main control unit circuit board.

In another embodiment, a white balance circuit is implemented as part of a digital signal processor (DSP) for video signals that is placed into an integrated circuit (DSP IC) or into the FPGA.

In another embodiment, a white balance circuit is implemented as part of a digital signal processor (DSP) for video signals that is built into a complementary metal oxide semiconductor (CMOS) video sensor.

In an embodiment, the present specification is directed toward a device for enabling uniform white balancing of a first viewing element and a second viewing element in an endoscopic tip, comprising: a housing defining an enclosed volume and having an opening for receiving said endoscopic tip, wherein said opening has a first diameter configured to snugly receive said endoscopic tip such that external light is prevented from entering through said opening when said endoscopic tip is inserted therein and wherein the enclosed volume has a surface area that is at a predefined distance from the second viewing element when said endoscopic tip is inserted therein; and a member extending out from the surface area and within the enclosed volume, wherein said member is configured to position said first viewing element at the predefined distance from the surface area.

The first viewing element and second viewing element each have a field of view, wherein the surface area of the enclosed volume within said first field of view of the first viewing element may be a first color, wherein the surface area of the enclosed volume within said second field of view of the second viewing element may be a second color, and wherein the first and second colors may be equal.

Further, a portion of the surface area of the enclosed volume within said second field of view may be at least 10 millimeters from the second viewing element.

In some embodiments, the enclosure comprises at least one indicator on said surface area, wherein said indicator is positioned on said surface area such that it is visible via said at least one side viewing element, indicating to a user that said tip is properly positioned within said enclosure.

The member may be a stopper component that extends inwardly from said surface area and is configured to contact a distal face of said endoscopic tip.

In an embodiment, the housing may comprise at least a first portion and a second portion which join together to form said housing.

In an embodiment, the device includes a coupling mechanism for securing said housing to a control unit of an endoscope system. The coupling mechanism may be at least one of a hanger or magnetic coupler.

In some embodiments, the enclosed volume has a cylindrical or spherical shape.

Further, the housing defining said enclosed volume may be of a second diameter which is equal to said first diameter plus twice said distance.

In another embodiment, the present specification is directed toward a white balancing system for enabling uniform white balancing of a first viewing element, a second viewing element, and a third viewing element in a tip of an endoscope, wherein the first viewing element is positioned on a distal face of said tip and the second and third viewing elements are positioned on sides of said tip, said white balancing system comprising: a housing defining an enclosed volume and having an opening for receiving said endoscopic tip, wherein said opening has a first diameter configured to snugly receive said endoscopic tip such that external light is prevented from entering through said opening when said endoscopic tip is inserted therein, wherein the enclosed volume has a surface area that is at a first predefined distance from the second viewing element and at a first predefined distance from the third viewing element when said endoscopic tip is inserted therein; and a member extending out from the surface area and within the enclosed volume, wherein said member is configured to position said first viewing element a second predefined distance from the surface area.

In an embodiment, the first predefined distance and second predefined distance may be the same or different.

Further, the white balance system may comprise a control unit connected to said endoscope and comprising a white balance circuit for white balance processing of images obtained by said first, second, and third viewing elements; and at least one display connected to said control unit for displaying said processed images.

The white balance enclosure includes, in some embodiments, a timer associated with said white balance circuit for controlling a time period of said white balance processing. The time period may be in the range of 3 to 5 seconds.

In some embodiments, the white balance enclosure further comprises a splitter associated with said white balance circuit for splitting a white balance command to a digital signal processor associated with each viewing element.

In an embodiment, the first viewing element, second viewing element, and third viewing element each have a field of view and wherein the surface areas of the enclosed volume within said fields of view comprise a white color.

In an embodiment, a portion of said surface area of the enclosed volume within a second field of view is at least 10 millimeters from the second viewing element and wherein a portion of said surface area of the enclosed volume within a third field of view is at least 10 millimeters from the third viewing element.

Further, the housing defining said enclosed volume may be of a second diameter which is equal to said first diameter plus twice said distance.

The member may be a stopper component that extends inwardly from said surface area and is configured to contact a distal face of said endoscopic tip.

In yet another embodiment, the present specification is directed toward a method for performing a white balance for images obtained from at least one front viewing element and at least one side viewing element of a tip of an endoscope, said method comprising: inserting a distal tip of said endoscope comprising said front viewing element and side viewing element into an enclosure, said enclosure comprising a three-dimensional body defining an inner area and having a proximal end, a distal end, an inner surface, an outer surface, a distal wall, and an opening at said proximal end; positioning said tip within said inner area of said enclosure such that said front viewing element and side viewing element are within said enclosure and each of said front and side viewing elements is positioned an equal distance from said inner surface of said enclosure; instructing a control unit to white balance said front and side viewing elements, wherein said control unit calculates white balance values using digital signal processors on said control unit and stores white balance values in memory to be used for later processing of images; and, removing said endoscope tip from said enclosure.

In accordance with an embodiment, a timer counts 3 to 5 seconds. A controller applies previously calibrated and stored white balance values/factors to selectively amplify or attenuate the respective red, green and blue or yellow, cyan, magenta, and green signals of each video feed. During the white balancing process, a digital signal processor (DSP) compares actual values of red, green, and blue or yellow, cyan, magenta, and green from the CCD or CMOS sensor, which are received from a white picture, with theoretical values of red, green, and blue or yellow, cyan, magenta, and green from a mathematical model of a white picture. Corrective parameters obtained from the comparison are used for red, green, and blue or yellow, cyan, magenta, and green adjustment amplifiers and are stored in a DSP memory. The white balanced signals are then displayed on one, two, or three monitors.

In one embodiment, a cap is designed to be conveniently slipped/slid onto and enclose the multiple viewing elements endoscopic tip. In alternate embodiments, the white balance enclosure is designed in the form of a clasp that securely encloses and attaches to the endoscopic tip, or in the form of a snap which snug-fits onto the endoscopic tip.

In alternate embodiments, the shapes of the first and second portions of the white balance enclosure are square or any other suitable shape that facilitates the endoscopic tip to be equidistant from the inner walls of the enclosure. Additionally, the first and second portions can be of different shapes—for example, the first inner portion can be cylindrical while the second inner portion is rectangular, square, or vice versa.

In accordance with an aspect of the present specification, the interior of the white balance enclosure is isolated from the influx of exterior light, to avoid creating uneven shadows and illumination in the interior of the enclosure and to prevent parasitic external illumination from non-endoscopic light sources/spectrums.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 6A is a perspective view of a white balance enclosure in accordance with an embodiment of the present specification;

FIG. 6B is another perspective view of a white balance enclosure in accordance with an embodiment of the present specification;

FIG. 6C is a cross-sectional view of one embodiment of a white balance enclosure showing the tip of a multi-viewing element endoscope positioned therein;

DETAILED DESCRIPTION

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It is noted that the term "endoscope" as mentioned to herein may refer particularly to a colonoscope and a gastroscope, according to some embodiments, but is not limited only to colonoscopes and/or gastroscopes. The term "endoscope" may refer to any instrument used to examine the interior of a hollow organ or cavity of the body.

Figure 1:
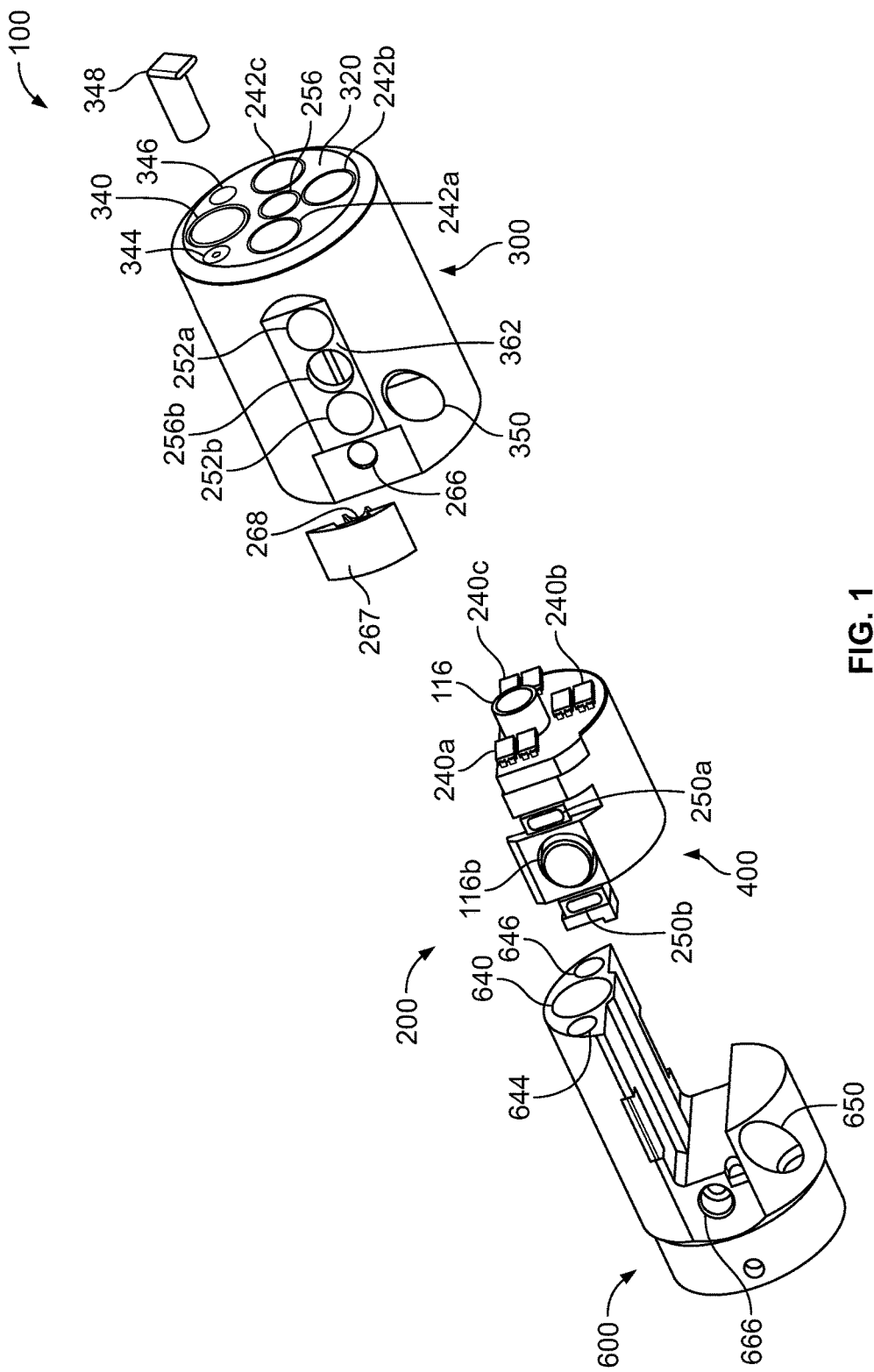
FIG. 1 shows an exploded view of a tip section of a multi-viewing elements endoscope, according to some embodiments.

Reference is now made to FIG. 1, which shows an exploded view of a tip section 200 of a multi-viewing elements endoscope assembly 100 according to an embodiment. An aspect of some embodiments relates to multi-viewing elements endoscope assembly 100 having tip section 200 equipped with one or more side service channels. Tip section 200 may be turned by way of flexible shaft (not shown), which may also be referred to as a bending section, such as, but not limited to a vertebra mechanism. According to an embodiment, tip section 200 of an endoscope includes a tip cover 300, an electronic circuit board assembly 400 and a fluid channeling component 600.

Electronic circuit board assembly 400 is, in one embodiment, configured to carry a front-looking viewing element 116, a first side-looking viewing element 116b and a second side-looking viewing element on the opposite side of the first side looking viewing element. The two side-looking viewing elements may be similar to front-looking viewing element 116 and may include a charge coupled device (CCD) or a complementary metal oxide semiconductor (CMOS) image sensor with optics.

Further, electronic circuit board assembly 400 is, in one embodiment, configured to carry front illuminators 240a, 240b, 240c, which are associated with and in communication with front looking viewing element 116, and are positioned to essentially illuminate the fields of view of front-looking viewing element 116.

In addition, electronic circuit board assembly 400 is, in one embodiment, configured to carry a first set of side illuminators 250a and 250b, which are associated with and in communication with side looking viewing element 116b, and are positioned to essentially illuminate the fields of view of side looking viewing element 116b. Electronic circuit board assembly 400 is, in one embodiment, also configured to carry a second set of side illuminators, which are associated with and in communication with a second side looking viewing element, which are similar to side illuminators 250a and 250b.

Front illuminators 240a, 240b, 240c, first set of side illuminators 250a and 250b, and the second set of side illuminators may optionally be discrete illuminators and may include a light-emitting diode (LED), which, in some embodiments, may be a white light LED, an infrared light LED, a near infrared light LED, an ultraviolet light LED or any other LED. In various embodiments, white balance is only possible for endoscopes using white light LEDs.

The term "discrete", concerning discrete illuminator, may refer to an illumination source which generates light internally, in contrast to a non-discrete illuminator, which may be, for example, a fiber optic merely transmitting light generated remotely.

Figure 2A:
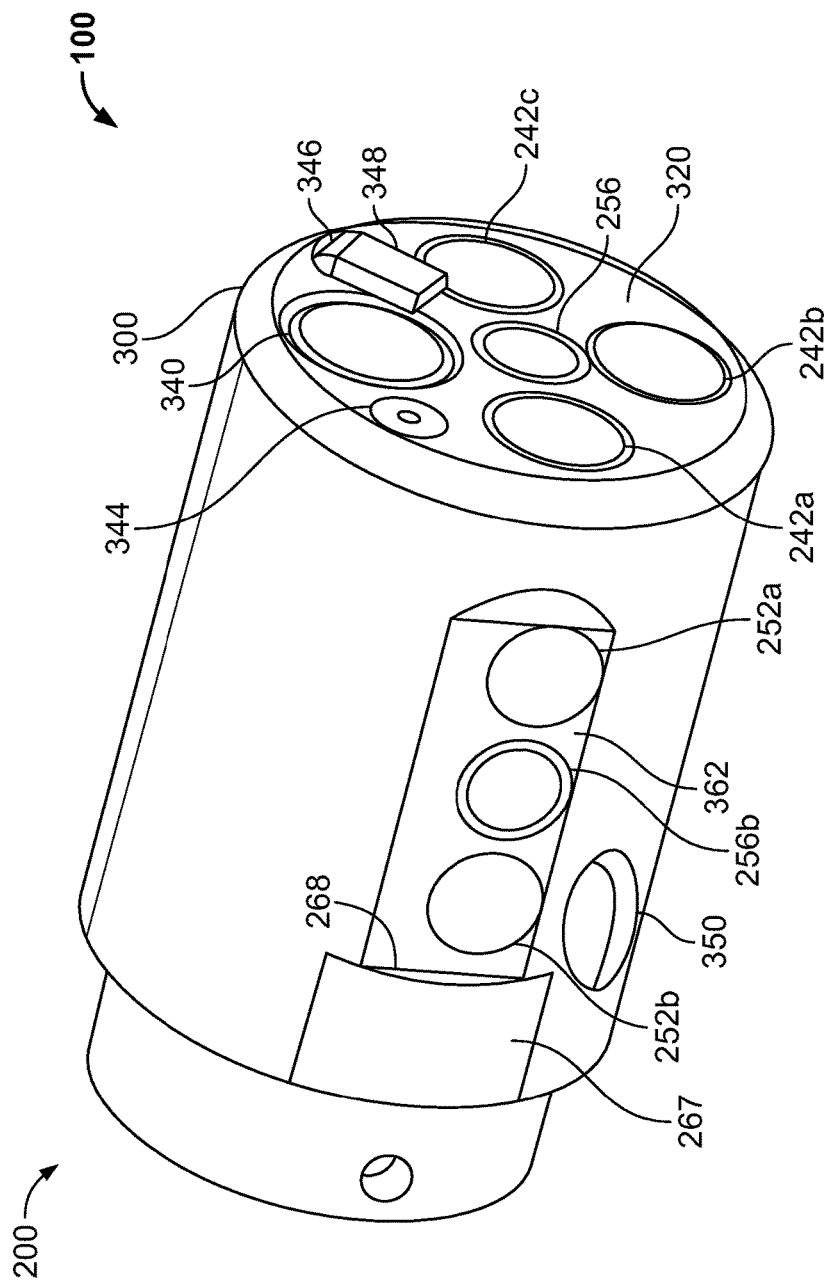
FIG. 2A shows a front perspective view of a tip section of a multi-viewing elements endoscope, according to some embodiments.
Figure 2B:
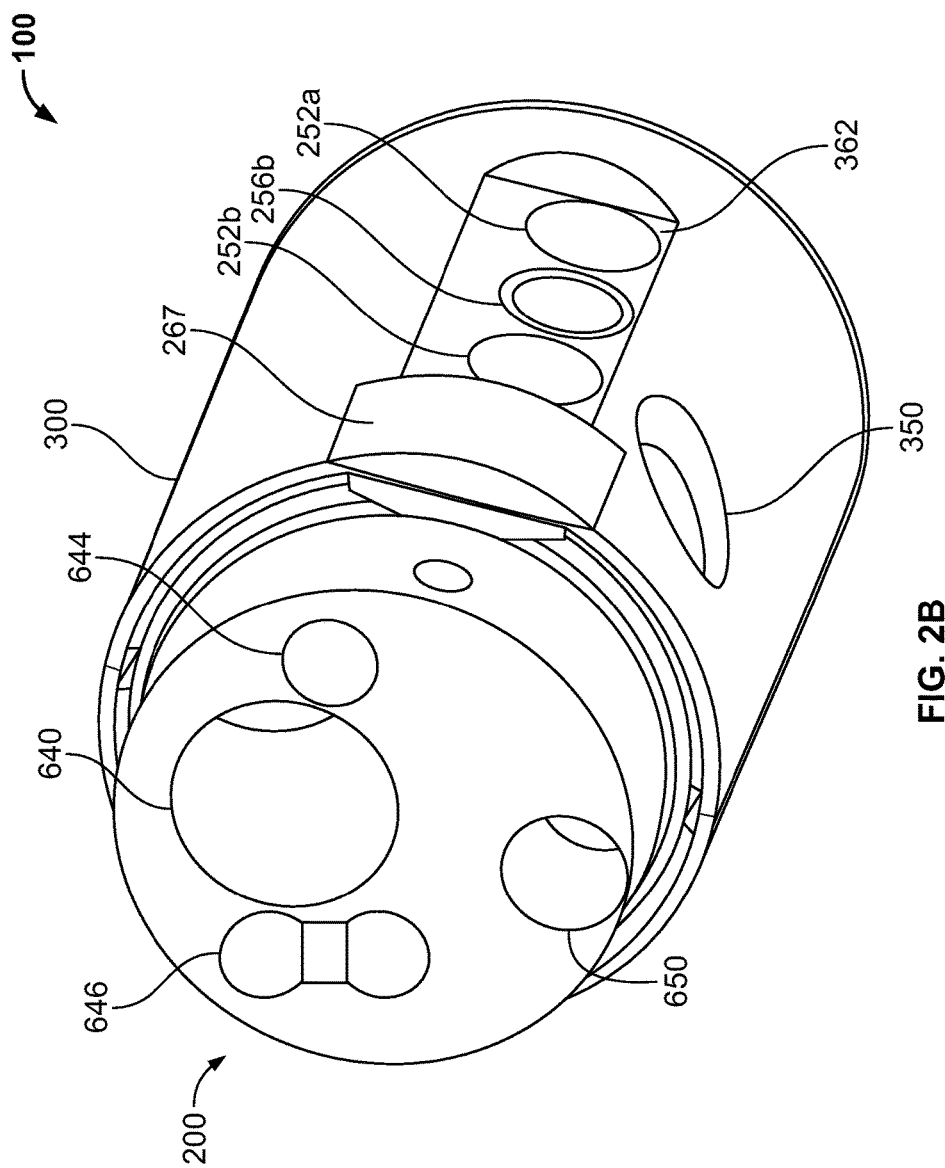
FIG. 2B shows a rear perspective view of a tip section of a multi-viewing elements endoscope, according to some embodiments.

Reference is now made to FIGS. 2A and 2B, which show a perspective view of a tip section 200 of a multi-viewing elements endoscope assembly 100 according to an embodiment. Tip cover 300 is configured to fit over the inner parts of the tip section 200 (including electronic circuit board assembly 400 and fluid channeling component 600 seen in FIG. 1), thus providing protection to the internal components housed within the inner parts. In some embodiments, tip cover 300 includes a front panel 320 having a front optical assembly 256, corresponding to front looking viewing element 116 seen in FIG. 1. Front optical assembly 256 includes a plurality of lenses (or, in one embodiment, the plurality of lenses is assembled on the CCD or CMOS), static or movable, which can provide a field of view of up to essentially 180 degrees. Front optical assembly 256, in one embodiment, can provide a focal length of up to approximately 110 millimeters.

Referring to FIGS. 1, 2A, and 2B simultaneously, the optical axis of front looking viewing element 116 is substantially directed along the long dimension of the endoscope. However, since front looking viewing element 116 is typically a wide angle viewing element, its field of view may include viewing directions at large angles with respect to its optical axis. Additionally, front panel 320 may include optical windows 242a, 242b and 242c of illuminators 240a, 240b and 240c, respectively. It should be noted that the number of illumination sources used for illumination of the field of view may vary in other embodiments.

In addition, front panel 320 may include a working channel opening 340 of a working channel 640, which is discussed in further detail below.

Jet channel opening 344 of jet channel 644 is, in one embodiment, located on front panel 320 of tip cover 300. Jet channel 644 may be configured for providing a high-pressure jet of fluid, such as water or saline, for cleaning the walls of the body cavity.

Also located on front panel 320 of tip cover 300 is injector opening 346 of injector channel 646 having a nozzle 348 aimed at front optical assembly 256. Injector channel 646 is configured, in one embodiment, to inject fluid (liquid and/or gas) to wash contaminants such as blood, feces and other debris from front optical assembly 256 of front looking viewing element 116. Optionally, in other embodiments, injector channel 646 is configured for cleaning front optical assembly 256 and one, two, or all of optical windows 242a, 242b, and 242c. Injector channel 646 may be fed by fluid such as water and/or gas, which can be used for cleaning and/or inflating a body cavity.

Side optical assembly 256b, corresponding to first side looking viewing element 116b, is, in one embodiment, located on sidewall 362 of tip cover 300 and is similar to front optical assembly 256. Further, sidewall 362 also houses optical windows 252a and 252b of illuminators 250a and 250b, corresponding to first side looking viewing element 116b. Also on the sidewall 362 of tip cover 300, on the opposing side to side optical assembly 256b, are an optical assembly and optical windows for a second side looking viewing element, which, in some embodiments, are similar to side optical assembly 256b and optical windows 252a and 252b of illuminators 250a and 250b corresponding to first side looking viewing element 116b. The white balance system of the present specification can be used with endoscopes having a front viewing element and one or more side viewing elements.

The optical axis of first side looking viewing element 116b is essentially oriented perpendicular to the long dimension of the endoscope. However, since side looking viewing element 116b is typically a wide angle viewing element, its field of view may include viewing directions at large angles relative to its optical axis.

In addition, side injector opening 266 of side injector channel 666 is located at the proximal end of sidewall 362 in one embodiment. Optionally, a nozzle cover 267 is configured to fit side injector opening 266. Additionally, nozzle cover 267 may include a nozzle 268 which is aimed at side optical assembly 256b and configured for injecting fluid to wash contaminants such as blood, feces and other debris from side optical assembly 256b of side looking viewing element 116b. The fluid may include gas, which is used for inflating a body cavity. Optionally, nozzle 268 can be configured for cleaning both side optical assembly 256b and optical windows 252a and/or 252b.

According to some embodiments, side injector channel 666 is configured to supply fluids for cleaning any of the tip elements (such as any optical assembly, windows, illuminators, and other elements). Optionally, injector channel 646 and side injector channel 666 are fed from the same fluid channel.

It is noted that according to some embodiments, although tip section 200 is presented herein showing one side thereof, the opposing side may include elements similar to the side elements described herein (for example, side looking viewing element, side optical assembly, injector(s), nozzle(s), illuminator(s), window(s), opening(s) and other elements).

In some embodiments, sidewall 362 forms of an essentially flat surface, which assists in directing the cleaning fluid injected from injector channel 666 toward side optical assembly 256b and optical windows 252a and/or 252b. Lack of such a flat surface may result in dripping of the cleaning fluid along the curved surface of tip section 200 of the endoscope, without performing the desired cleaning action.

It is noted that according to some embodiments, tip section 200 may include more than one side looking viewing element. In this case, the side looking viewing elements may be installed such that their field of views are substantially opposing. However, different configurations and a varied number of side-looking viewing elements are possible within the general scope of the current specification.

According to some embodiments, there is provided herein an endoscope (such as but not limited to a colonoscope and/or gastroscope) that includes (in a tip section thereof), in addition to a front viewing element and one or more side viewing elements, and in addition to a front working channel that is configured for insertion of a medical (such as surgical) tool, optionally, at least one side service channel that is configured for insertion of a medical tool. Thus, in one embodiment, the fluid channeling component includes a side service channel 650 having a side service channel opening 350.

Figure 3:
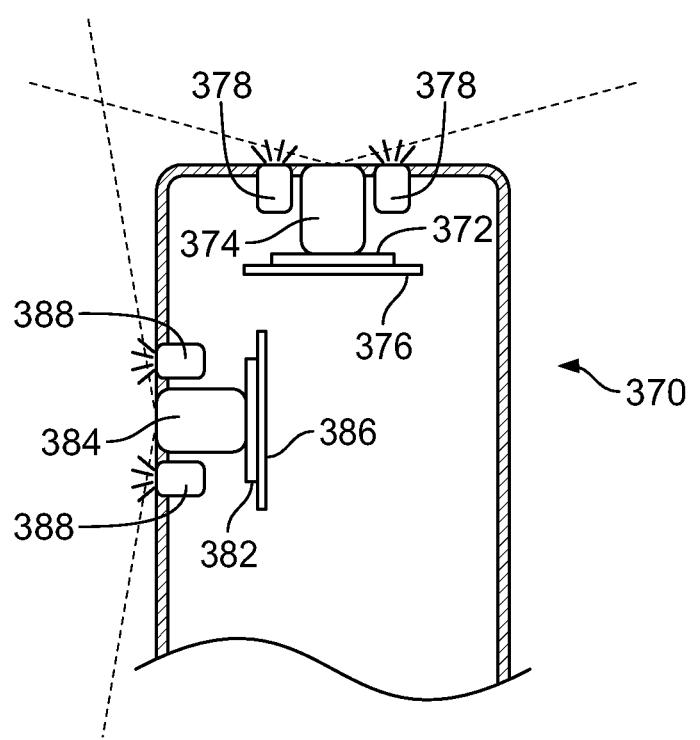
FIG. 3 shows a cross-sectional view of a tip section of a multi-viewing elements endoscope, according to some embodiments.

Reference is now made to FIG. 3, which, in accordance with an embodiment, shows a cross-sectional view of a tip section 370 of a multi-viewing elements endoscope. Tip section 370 includes a front-pointing image sensor 372, such as a charge coupled device (CCD) or a complementary metal oxide semiconductor (CMOS) image sensor. Front-looking image sensor 372 is, in one embodiment, mounted on a printed circuit board 376, which may be rigid or flexible. Printed circuit board 376 is configured to supply front-looking image sensor 372 with necessary electrical power and signals such as clock, synchronization, etc., and to derive still images and/or video feeds captured by the image sensor. Printed circuit board 376 is connected to a set of electrical cables which, in one embodiment, is threaded through an electrical channel running through the elongated shaft of the endoscope. Front-looking image sensor 372 and a lens assembly 374, which in one embodiment, is mounted on top of image sensor 372, provide the necessary optics for receiving images. Lens assembly 374 may include a plurality of lenses, static or movable, for providing a field of view of at least 90 degrees and up to essentially 180 degrees. Front-looking image sensor 372 and lens assembly 374, with or without printed circuit board 376, may be jointly referred to as a "front-looking viewing element".

One or more discrete front illuminators 378 are, in some embodiments, placed next to lens assembly 374 for illuminating its field of view. Optionally, discrete front illuminators may be attached to the same printed circuit board on which the front-pointing image sensor is mounted.

Optionally, tip section 370 further includes a side-looking image sensor 382, such as a charge coupled device (CCD) or a complementary metal oxide semiconductor (CMOS) image sensor. Side-looking image sensor 382 is, in one embodiment, mounted on a printed circuit board 386, which may be rigid or flexible. Printed circuit board 386 is configured to supply side-looking image sensor 382 with necessary electrical power and signals such as clock, synchronization, etc., and to derive still images and/or video feeds captured by the image sensor. Side-looking image sensor 382 and a lens assembly 384, which in one embodiment, is mounted on top of image sensor 382, provide the necessary optics for receiving images. Side-looking image sensor 382 and lens assembly 384, with or without printed circuit board 386, may be jointly referred to as a "side looking viewing element".

One or more discrete side illuminators 388 are, in some embodiments, placed next to lens assembly 384 for illuminating its field of view. Optionally, discrete front illuminators may be attached to the same printed circuit board on which the side-looking image sensor is mounted.

In another configuration, the printed circuit boards employed in the present specification may optionally be a single printed circuit board on which both front and side-looking image sensors are mounted. For this purpose, the printed circuit board is essentially L-shaped.

Front and side-looking image sensors 372 and 382 may be similar or identical in terms of, for example, field of view, resolution, light sensitivity, pixel size, focal length, focal distance and/or the like. Further, there may be two side-pointing image sensors in other embodiments.

Optionally, side-looking image sensors and their respective lens assemblies are advantageously positioned relatively close to the distal end surface of tip section 370. For example, a center of the side-looking viewing element (which is the center axis of side-looking image sensor 382 and lens assembly 384) is positioned approximately 7 to 11 millimeters from the distal end surface of the tip section. This is enabled by an advantageous miniaturizing of the front and side-looking viewing elements which allows for enough internal space in the tip section for angular positioning of the viewing elements without collision. Persons of ordinary skill in the art should note that in accordance with an embodiment, the multi-viewing elements endoscope comprises one, two, or more than two side-looking viewing elements along with a front-looking viewing element.

Figure 4:
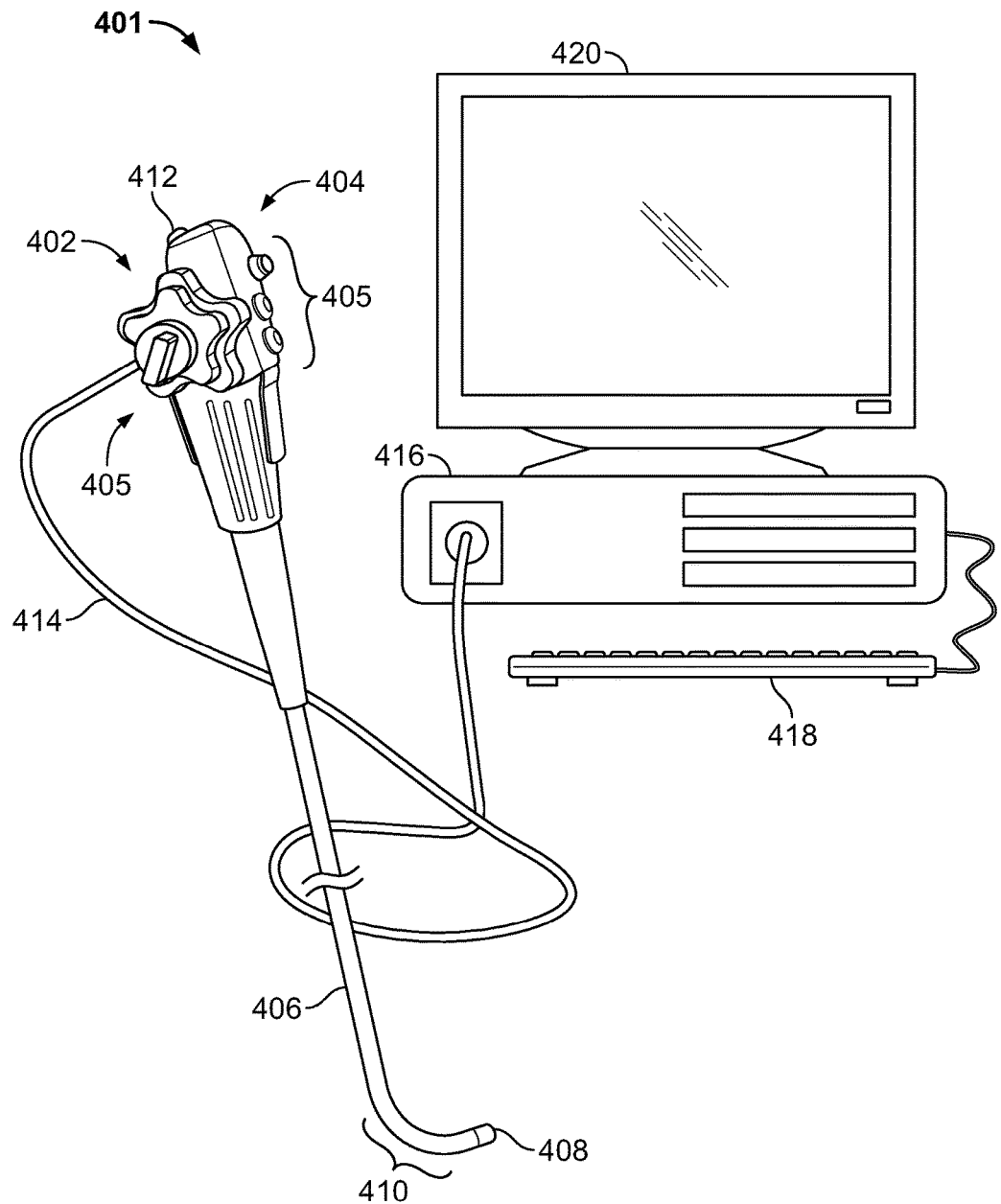
FIG. 4 shows a multi-viewing elements endoscopy system, according to some embodiments.

Reference is now made to FIG. 4, which shows a multi-viewing elements endoscopy system 401. In one embodiment, system 401 includes a multi-viewing elements endoscope 402. Multi-viewing elements endoscope 402 may include a handle 404, from which an elongated shaft 406 emerges. Elongated shaft 406 terminates with a tip section 408, such as that described with respect to FIGS. 1, 2A, and 2B, which can be maneuvered by way of a bending section 410. Handle 404 is used for maneuvering elongated shaft 406 within a body cavity; the handle may include one or more knobs and/or switches 405 which control bending section 410 as well as functions such as fluid injection and suction. Handle 404 may further include a working channel opening 412 through which surgical tools may be inserted as well as one or more side service channel openings.

A utility cable 414 is used to connect handle 404 and a main control unit 416. In an embodiment, utility cable 414 includes therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators. In some embodiments, the electrical channel(s) also include cables for clocking and synchronization signals and a cable for control of the CCD or CMOS image sensors. In various embodiments, the above functions are combined into one cable or separated into multiple cables.

The main control unit 416 governs a plurality of operational functionalities of the endoscope. For example, the main control unit 416 may govern power transmission to the tip section 408 of endoscope 402, such as for the tip section's viewing elements and illuminators. The main control unit 416 may further control one or more fluid, liquid and/or suction pumps, which supply corresponding functionalities to endoscope 402. One or more input devices, such as a keyboard 418, can be connected to main control unit 416 for the purpose of human interaction with the main control unit 416. In another configuration, an input device, such as a keyboard, may optionally be integrated with the main control unit in a same casing.

A display 420 can be connected to main control unit 416 and configured to display images and/or video streams received from the viewing elements of multi-viewing elements endoscope 402. Display 420 is optionally configured to display a user interface for allowing a human operator to set various features of system 401.

Optionally, the video streams received from the different viewing elements of multi-viewing elements endoscope 402 can be displayed separately on display 420, either side-by-side or interchangeably (particularly, the operator may switch between views from the different viewing elements manually). Alternatively, these video streams may be processed by main control unit 416 to combine them into a single, panoramic video frame, based on an overlap between fields of view of the viewing elements.

In another optional configuration, two or more displays may be connected to main control unit 416, each for displaying a video stream from a different viewing element of the multi-viewing elements endoscope 402.

Figure 5A:
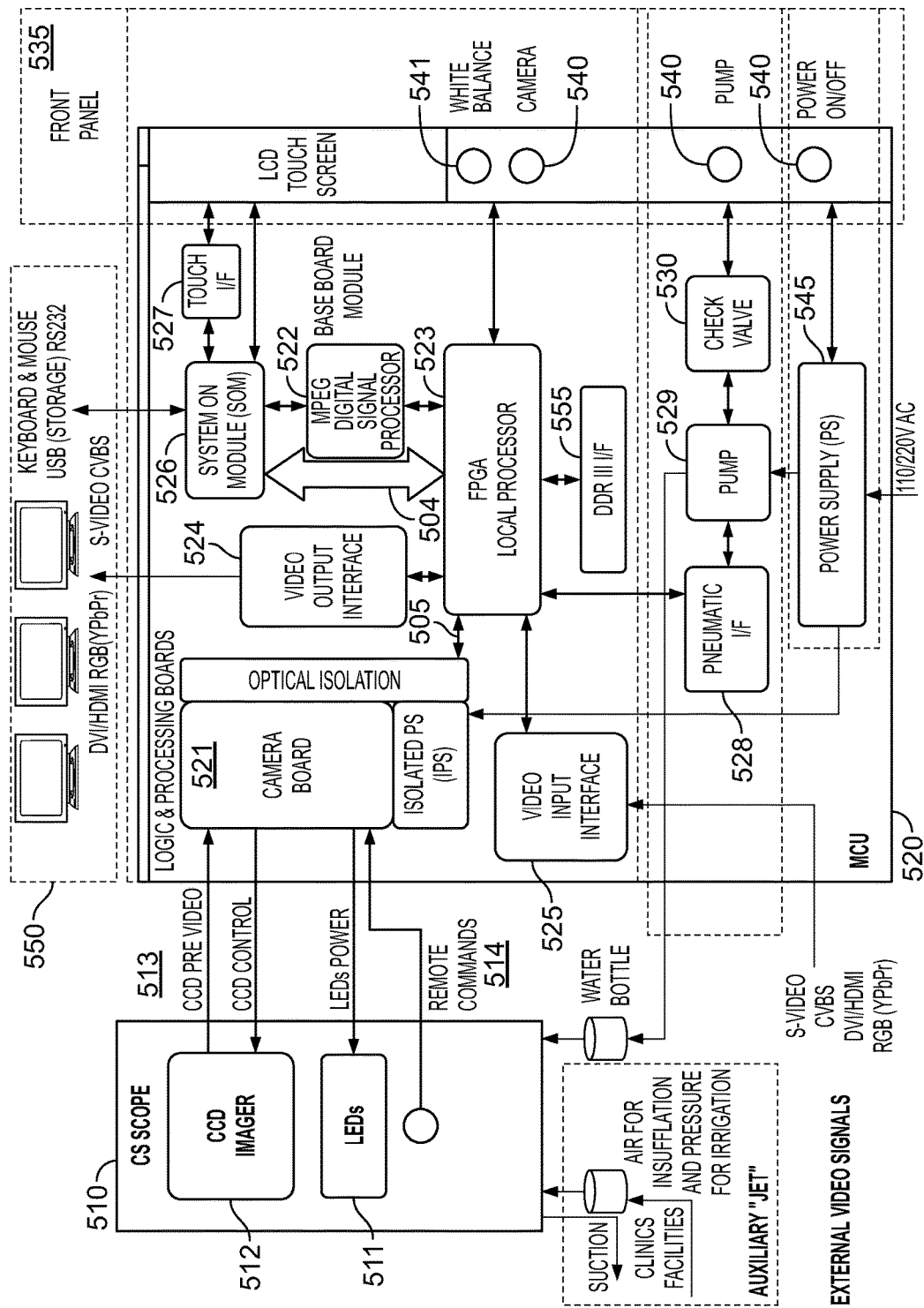
FIG. 5A is a block diagram illustrating one embodiment of an overall video processing architecture.

FIG. 5A is a flow diagram detailing how a controller unit 520 of the main control unit operatively connects with the endoscope 510 and the display units 550. Display units 550 are described above with respect to FIG. 4 as display 420. Referring to FIG. 5A, controller unit 520 comprises a camera board 521 that transmits appropriate commands to control the power supply to the LEDs 511 and to control the operation of image sensor 512 (comprising one or more viewing elements), such as a charge coupled device (CCD) as shown in FIG. 5A or, in other embodiments, a complementary metal oxide semiconductor (CMOS) imager, located within the endoscope of the present specification. The camera board 521, in turn, receives at least one video signal 513 generated by the image sensor 512 and optionally other remote commands 514 from the endoscope.

U.S. patent application Ser. No. 14/263,896, entitled "Video Processing In A Compact Multi-Viewing Element Endoscope System" and filed on Apr. 28, 2014 and U.S. Provisional Patent Application No. 61/936,562, entitled "Method and System for Video Processing in a Multi-Viewing Element Endoscope", filed on Feb. 6, 2014 describes the remote commands and associated video processing signals and are herein incorporated by reference in their entirety.

Controller unit 520 further comprises components for processing the video obtained from the image sensor 512, including MPEG digital signal processor 522 and field-programmable gate array (FPGA) local processor 523 that performs video interpolation and on-screen display overlay. The video signal is sent for display through video output interface 524. A video input interface 525 is also provided for receiving video input from an external analog or digital video source.

System on module (SOM) 526 provides an interface for input devices such as a keyboard and mouse, while touch I/F 527 provides touch-screen interface functionality. Controller unit 520 may further control one or more fluid, liquid and/or suction pump(s) which supply corresponding functionalities to endoscope 510 through pneumatic I/F 528, pump 529, and check valve 530. Controller unit 520 further comprises a power supply on board 545 and a front panel 535, which provides operational buttons 540 and switch 541 for the user.

Camera board 521 receives video signal 513 which, in one embodiment, comprises three video feeds, corresponding to video pickups by three endoscopic tip viewing elements (one front and two side-looking viewing elements), as generated by image sensor 512.

Figure 5B:
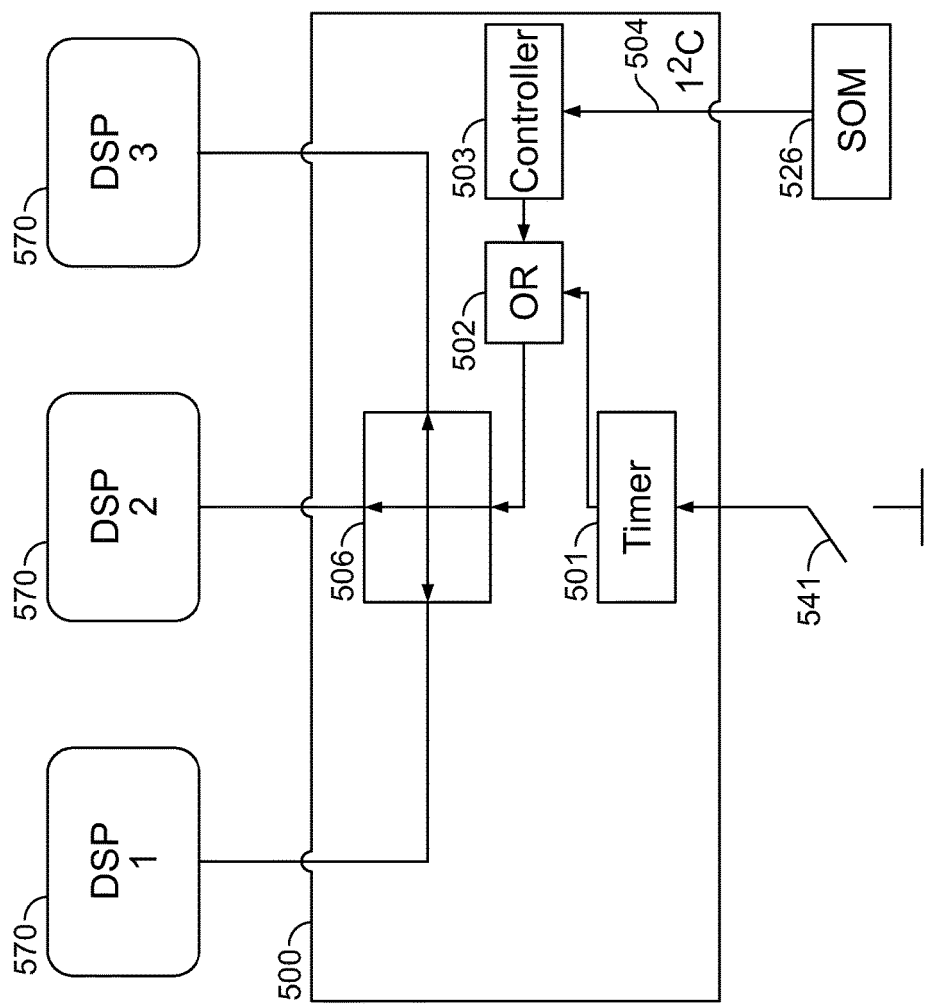
FIG. 5B is a block diagram illustrating an embodiment of a white balancing circuit.

FIG. 5B shows a block diagram of an embodiment of a white balance circuit 500 that is implemented as part of the controller unit 520 of FIG. 5A. Referring now to FIGS. 5A and 5B, a plurality of video digital signal processors (DSPs) 570, either placed on camera board 521 or built into a CMOS sensor, receive a "white balance command" through element OR 502. A "white balance command" is either produced by a timer 501 which is controlled by an operator (physician) through a momentary electrical switch 541 or produced by a controller 503 with a built-in timer configured to receive commands from system-on-module (SOM) 526. The commands are provided through a multi-master serial single ended computer bus 504, which, in various embodiments, comprises an Inter-Integrated Circuit (I²C) or other standard bus communication, including parallel. In one embodiment, the "white balance command" is only operator initiated. In various embodiments, the white balance time period is typically a few seconds, such as 3-5 seconds, and can be other time periods dependent upon the DSP.

Persons of ordinary skill in the art would appreciate that each of the three video feeds 505 includes color image information comprising the three primary color image signals—red (R), green (G), and blue (B), or four additional color image signals—yellow (Ye), cyan (Cy), magenta (Mg), and green (G), for reproducing a color image.

For generating calibrated white balance values/factors, in one embodiment, the three endoscopic tip viewing elements (one front and two side-looking viewing elements) are directed to image a reference white object to obtain/calculate baseline or reference white balance values/factors $W_R$, $W_G$, $W_B$ for the corresponding three primary colors or $W_{Ye}$, $W_{Cy}$, $W_{Mg}$, $W_G$ for the corresponding four additional colors. In accordance with an aspect of the present specification, a novel white balance enclosure (described below with reference to FIGS. 6A, 6B, 6C, 6D, and 6E) is used as a reference white object to consistently and uniformly white balance each of the three viewing elements of the endoscope. The endoscopic tip is inserted into the white balance enclosure and the three viewing elements of the endoscope, along with the corresponding illuminators, are placed in operation, described in detail in the following paragraph, to expose the three endoscopic tip viewing elements to a uniform white surrounding, thus generating three corresponding test feeds. While described for an endoscope comprising three viewing elements, the white balancing process described herein can be used for an endoscope having any number of viewing elements.

Referring back to FIGS. 5A and 5B, after exposing the viewing elements uniformly to the reference white surrounding, white balance switch 541 (located on the front panel 535 of the main control unit) is pressed to activate or cause the DSPs 570 to calculate white balance values/factors $W_R$, $W_G$, $W_B$ or $W_{Ye}$, $W_{Cy}$, $W_{Mg}$, $W_G$ corresponding to the three primary colors or four additional color respectively, for each of the three test feeds. The white balance values/factors are then stored in an electronic memory element 555, such as electrically erasable programmable read-only memory (EEPROM). Persons of ordinary skill in the art would appreciate that the white balancing is directed to and performed on both still images as well as video signals generated by the viewing elements of the endoscope. In other words, the aforementioned test feeds comprise both still images as well as video signals.

In accordance with one embodiment, the white balance process is performed by the DSPs 570. A white balance signal is a command for the DSPs 570 to perform white balance processing and is sent from the white balance circuit 500 to the plurality of DSPs 570 through a splitter element 506. The previously calculated and stored white balance values/factors $W_R$, $W_G$, $W_B$ or $W_{Ye}$, $W_{Cy}$, $W_{Mg}$, $W_G$ are sent to the DSPs 570 to independently amplify or attenuate the respective red, green, and blue signals or yellow, cyan, magenta, and green signals of each of the three video feeds 505 received by the white balance circuit.

Figure 6D:
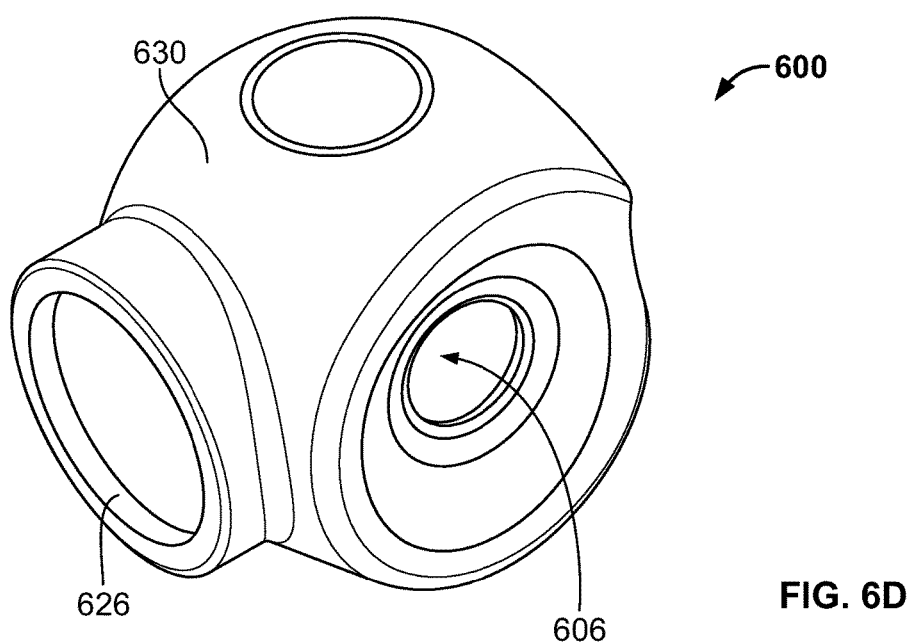
FIG. 6D is yet another perspective view of a white balance enclosure in accordance with an embodiment of the present specification.

FIGS. 6A, 6B, 6D and 6E are perspective views of a white balance enclosure 600 of the present specification, while FIG. 6C is a cross-sectional view of a white balance enclosure 600 showing a multiple viewing elements endoscopic tip 620 positioned therein. Referring now to FIGS. 6A through 6E, in accordance with an embodiment, enclosure 600 is internally designed as a cap (to conveniently slip/slide onto, be positioned over, and enclose the multiple viewing elements endoscopic tip 620) comprising first body portion or front portion 605 and second body portion or housing 610 that, in one embodiment, are substantially cylindrical. Portions 605, 610 are of similar, identical, or different shapes, such as and not limited to rectangular, square, or any other shape. It should also be noted that while the present specification describes the white balance enclosure as being comprised of body portions, the enclosure may form a single, integrated body unit.

The second body portion 610, in one embodiment, is a housing defining an enclosed volume that has an opening 606, defined by at least partially coaxial first body portion 605, for receiving the endoscopic tip. In one embodiment, the opening 606 has a circumference or diameter that is configured to snugly receive the endoscopic tip such that external light is prevented from entering through the opening 606. The enclosed volume of the housing has a surface area that is located at a pre-defined distance from at least one second viewing element. Further, the enclosed volume of the housing includes a member extending from the surface area (and positioned thereupon) to position the first viewing element at a predefined distance from the surface area.

In one embodiment, first portion 605 is positioned at, and housed at least partially coaxially within, a front area of second portion 610. First portion 605 defines an opening 606, having a first diameter 'd', which leads into an inner area of second portion 610, having a second diameter 'D'. In one embodiment, the inner area is substantially cylindrical or spherical for receiving the endoscope tip. The distal end of second portion 610 is closed with a distal wall 611. The first diameter 'd' is configured to enable a multi-viewing elements endoscope tip 620, such as a two viewing elements (one front and one side-looking viewing element) or a three viewing elements (one front and two side-looking viewing elements) endoscopic tip, to be conveniently inserted through and fit snugly into opening 606 and into a front area of the second portion 610. The diameter 'D' is configured to ensure that once the endoscopic tip 620 lies within second portion 610, the distance of endoscopic tip 620 (and therefore the multiple viewing elements) from the inner surfaces of second portion 610, including the distal wall 611, is equal to 't'. Therefore, in accordance with an embodiment, the relationship of the two dimensions 'd' and 'D' (respective 'diameters' for the first and second portions 605, 610 in accordance with an embodiment) of the two portions 605, 610, respectively, is defined as D=d+2t. In various embodiments, the distance 't' ranges from 10 to 12 millimeters. In one embodiment, the distance 't' is larger than 12 millimeters.

In one embodiment, at least a portion of the surface area of the enclosed volume that is within the field of view of the second viewing element is at least 10 millimeters.

Persons of ordinary skill in the art would appreciate that the dimensional relationship between the respective dimensions of the first and second portions 605 and 610 ensures that portions of the outer surface of tip 620 lies at distance 't' from the inner walls of second portion 610. Thus, the side-looking viewing elements located on the outer cylindrical side surface of endoscopic tip 620 and the front-looking viewing element located at the leading surface or distal face 615 of endoscopic tip 620 are maintained at a substantially uniform distance 't' from the inner walls of second portion 610.

An optional indicator marking 612 further facilitates/aids a leading surface or distal face 615 of endoscopic tip 620, and therefore the front-looking viewing elements situated thereon, to be maintained at a substantially uniform distance 't' from distal wall 611. In some embodiments, the indicator marking 612 is a thin line engraved or embossed into the inner walls of second portion 610. In one embodiment, the indicator 612 is marked at a position such that when the side-looking viewing elements of tip 620 captures a view of the indicator, it should be understood by the user of the endoscope that leading surface 615 is positioned at an appropriate distance 't' from distal wall 611. In another embodiment, the inner walls of second portion 610, including distal wall 611, has posts, protrusions, or stopper component(s) 613 that are positioned to meet endoscopic tip 620 at its edges. Thus, positioning of tip 620 at a proper distance 't' from the inner walls is facilitated by the use of physical structures, however, at the same time the viewing elements and illuminators and corresponding fields of view remain unhindered (the fields of view are not blocked).

In one embodiment, the inner surface are of the enclosure of the present specification is of a uniform color. In other embodiments, the inner surface area of the enclosure facing the fields of view of the first and second viewing elements is the same color. In other embodiments, the inner surface area of the enclosure facing the field of view of the first viewing element is of a first color and the inner surface area of the enclosure facing the field of view of the second viewing element is of a second color.

In one embodiment, once tip 620 is inserted into enclosure 600, the inner walls of second portion 610 and distal wall 611 together provide a uniform reference white surrounding/background to the multiple viewing elements of endoscopic tip 620. Also, since each viewing element of tip 620 is situated at a substantially uniform distance 't' from the white background, this facilitates simultaneous, consistent, and uniform white balancing of all of the multiple viewing elements of tip 620. Additionally, once tip 620 is positioned within enclosure 600, the interior of enclosure 600 can be isolated from the influx of exterior light, so as to avoid creating uneven shadows and illumination in the interior of enclosure 600. In one embodiment, enclosure 600 is made from a thermoplastic elastomer (TPE) and/or a thermoset elastomer to ensure an optimally light yet robust structure.

In one embodiment, enclosure 600 is an enclosure that can be slipped/slid onto endoscopic tip 620. In alternative embodiments, enclosure 600 is designed in the form of: a clasp that securely encloses and attaches to endoscopic tip 620; a snap which snug-fits onto endoscopic tip 620; or any other such suitable insertion structure that would be advantageously evident to those of ordinary skill in the art. Also, while in one embodiment enclosure 600 comprises cylindrical first and second portions 605, 610, in alternative embodiments, the shape of the first and second portions 605, 610 is rectangular, square or any other suitable shape that facilitates positioning of endoscopic tip 620 (and therefore the front and side-looking viewing elements thereon) to be equidistant from the inner walls of enclosure 600. Additionally, first and second portions 605 and 610 can be of different shapes—for example, first portion 605 can be cylindrical while second portion 610 is rectangular, square, or vice versa.

Figure 6E:
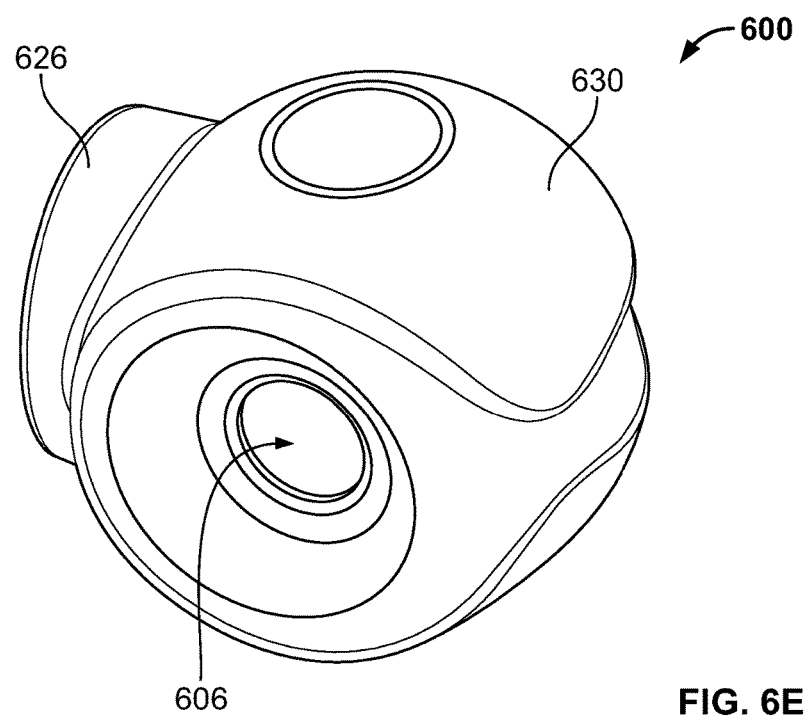
FIG. 6E is still another perspective view of a white balance enclosure in accordance with an embodiment of the present specification.

An outer surface 630 of second portion 610 comprises a connector that, in one embodiment, is a hanger 625 as shown in FIGS. 6A and 6B. In another embodiment, the connector is a coupler 626 as shown in FIGS. 6D and 6E. When not in use, enclosure 600 is removably attached to a side of the main control unit (such as main control unit 416 shown in FIG. 4) by mating hanger 625 with a corresponding plug located on the side of the main control unit, in accordance with an embodiment. In various embodiments, hanger 625 connects with the corresponding plug by structurally engaging with the plug or magnetically coupling with the plug. In another embodiment, enclosure 600 is integrated to a side of the main control unit (such as the main control unit 416 shown in FIG. 4) by coupler 626. In one embodiment, when the white balance enclosure is connected to the main control unit via coupler 626, it is fixedly attached. The endoscope is inserted into the white balance enclosure when attached and the calibration ensues. Persons of ordinary skill in the art should appreciate that while the enclosure 600 is internally designed as a cap, in one embodiment, outer surface 630 can have any shape, size and dimensions as would be ergonomically advantageous. In other embodiments, the white balance enclosure may reside within the main control unit such that it is an integral part of the unit.

Figure 7:
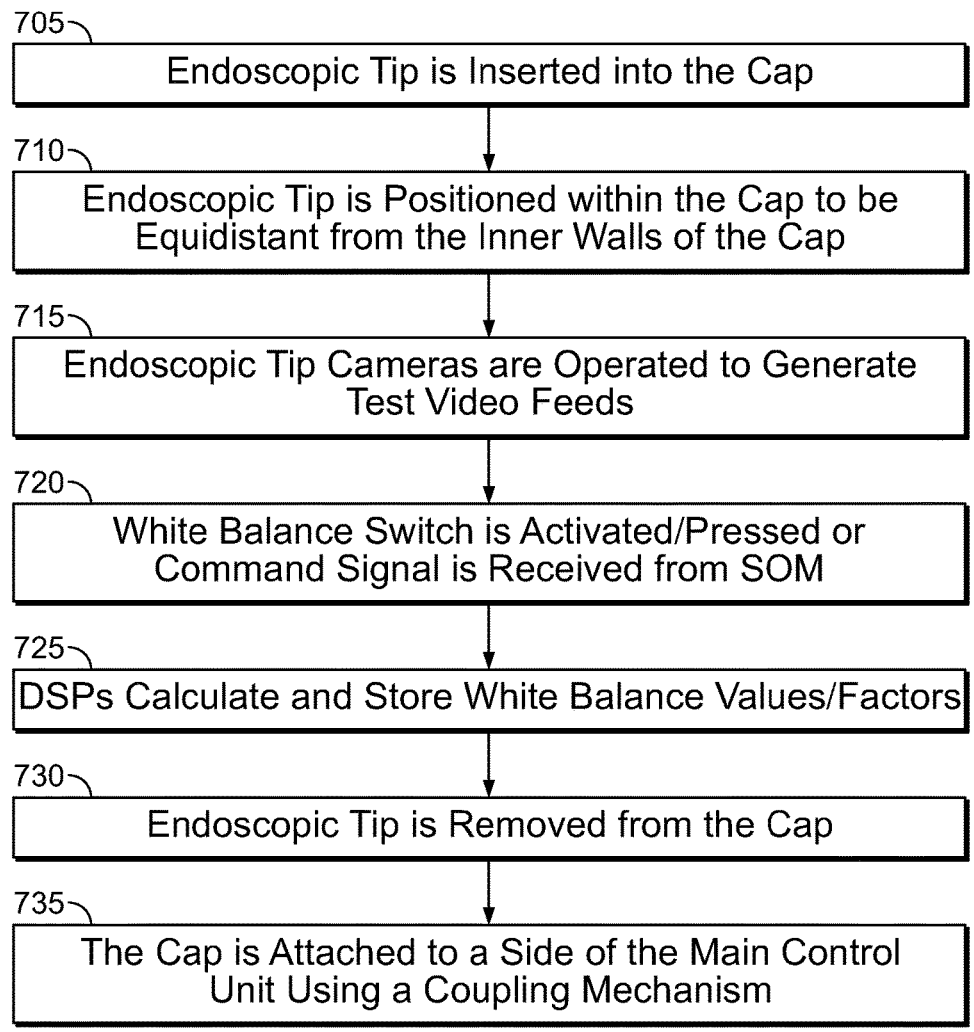
FIG. 7 is a flow diagram showing exemplary steps of one embodiment of using the white balance enclosure to calibrate/white balance multiple viewing elements of an endoscope.

FIG. 7 is a flow diagram showing exemplary steps of one embodiment of using the white balance enclosure, internally designed as a cap in accordance with an embodiment (and hereinafter referred to as the 'cap'), to simultaneously, uniformly, and consistently calibrate/white balance multiple viewing elements of an endoscopic tip. At 705, for white balancing, a physician or other operator of the endoscopic device inserts the multi-viewing elements endoscopic tip (such as an endoscopic tip comprising three viewing elements—one front-looking and two side-looking) through an opening of the cap. At 710, the physician ensures that the endoscopic tip is positioned within the cap such that the endoscopic tip is substantially equidistant from inner walls as well as a distal wall of the cap. At 715, the multiple viewing elements, along with corresponding illuminators, are activated using appropriate input commands to expose the multiple viewing elements simultaneously, uniformly, and consistently to a reference white surrounding within the cap. The image/video processing system generates white fields (test feeds) corresponding to each of the multiple viewing elements. Thereafter, at 720, the white balance switch, located on a front panel of a main control unit, is pressed/activated by the operator (input received from the system-on-module SOM) or activated by a predetermined command signal to perform a white balance. At 725, digital signal processors (DSPs) calculate and store white balance values/factors $W_R$, $W_G$, $W_B$ or $W_{Ye}$, $W_{Cy}$, $W_{Mg}$, $W_G$ corresponding to the three primary colors (Red, Green and Blue) or four additional colors (Yellow, Cyan, Magenta, and Green) for the test feeds of each multiple viewing element. At 730, the operator removes the endoscopic tip from the white balance enclosure. After use, at 735, the white balance enclosure is placed along the main control unit. The cap/enclosure is coupled to a side of the main control unit using a coupling mechanism, such as a hanger. The hanger may be attached to the cap or to the main control unit.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

In the description and claims of the application, each of the words "comprise" "include" and "have", and forms thereof, are not necessarily limited to members in a list with which the words may be associated.

We claim:

1. A method for white balancing of a first viewing element and a second viewing element in a tip of an endoscope, wherein the first viewing element is positioned on a distal face of the tip and the second viewing element is positioned on a side of the tip, the method comprising:
   inserting the endoscope tip into a housing, the housing including an opening leading into an enclosed volume, wherein the opening is configured to receive the endoscope tip such that external light is prevented from entering through the opening when the endoscope tip is inserted therein, and such that a field of view of the first viewing element and a field of view of the second viewing element are only of an interior of the housing, wherein the endoscope tip is isolated from any influx of external light when positioned within the housing;
   wherein the endoscope tip is inserted into the housing via the opening;
   positioning the first viewing element at a first predefined distance from a first interior surface of the housing;
   white balance processing images obtained by the first viewing element and the second viewing element; and
   splitting a white balance command to a digital signal processor associated with said first viewing element and said second viewing element.

2. The method of claim 1 further comprising displaying said images.

3. The method of claim 1 comprising connecting a control unit to the endoscope, wherein the control unit comprises:
   a white balance circuit for the white balance processing of images obtained by the first and second viewing elements; and
   a splitter associated with the white balance circuit for splitting the white balance command to the digital signal processor associated with said first viewing element and said second viewing element.

4. The method of claim 1, further comprising controlling a time period of the white balance processing.

5. The method of claim 4, wherein the time period is in a range from 3 to 5 seconds.

6. The method of claim 1, wherein, upon positioning the first viewing element at the first predefined distance from the first interior surface of the housing, the second viewing element is positioned at a second predefined distance from a second interior surface of the housing.

7. The method of claim 6, wherein the first predefined distance and second predefined distance are the same.

8. The method of claim 6, wherein the first predefined distance and second predefined distance are different.

9. The method of claim 1, wherein the portion of the first interior surface of the housing within the field of view of the first viewing element is a first color, wherein a portion of a second interior surface of the housing within the field of view of the second viewing element is a second color.

10. The method of claim 9, wherein the first and second colors are the same.

11. The method of claim 9, wherein the portions of the first and second interior surfaces of the housing within the fields of view of the first viewing element and second viewing element have a white color.

12. The method of claim 9, wherein a portion of the second interior surface of the housing is at least 10 millimeters from the field of view of the second viewing element.

13. The method of claim 1, further comprising positioning the endoscope tip within the opening using at least one indicator on a second interior surface of the housing, wherein the indicator is positioned on the second interior surface of the housing such that the at least one indicator is visible via the second side viewing element.

14. The method of claim 1, further comprising forming the housing by joining together a first portion of the housing and a second portion of the housing.

15. The method of claim 1, wherein the interior of the housing has a cylindrical or spherical shape.

16. The method of claim 1, wherein the opening has a first diameter and wherein the enclosed volume is defined by a second diameter equal to the first diameter plus twice the first predefined distance.

17. The method of claim 1 further comprising white balance processing of images obtained by a third viewing element positioned on a side of the tip of the endoscope, wherein the housing has a third interior surface that is at the first predefined distance from the third viewing element when the tip of the endoscope is inserted into the opening.

18. A method for white balancing of a first viewing element and a second viewing element in a tip of an endoscope, wherein the first viewing element is positioned on a distal face of the tip and the second viewing element is positioned on a side of the tip, wherein the endoscope tip includes a cover with a cylindrical wall, a distal end wall at an end of the cylindrical wall, and openings in at least one of the cylindrical wall and the distal end wall for the first viewing element and the second viewing element, the method comprising:

inserting the endoscope tip, including at least a portion of the cover, into a housing, the housing including an opening leading into an enclosed volume, wherein the opening is configured to receive the endoscope tip such that external light is prevented from entering through the opening when the endoscope tip is inserted therein, and such that a field of view of the first viewing element and the field of view of the second viewing element are only of an interior of the housing, wherein the endoscope tip is isolated from any influx of external light when positioned within the housing;

wherein the endoscope tip is inserted into the housing via the opening; and white balance processing images obtained by the first viewing element and the second viewing element.

\* \* \* \* \*